(12) United States Patent
Watarai et al.

(10) Patent No.: US 7,642,512 B2
(45) Date of Patent: Jan. 5, 2010

(54) MASS SPECTROMETRY AND MASS SPECTROSCOPE

(75) Inventors: Hitoshi Watarai, Toyonaka (JP); Hideaki Monjushiro, Takatsuki (JP); Katsuya Watanabe, Yamato (JP); Masayori Suwa, Katano (JP); Mariko Arase, Toyonaka (JP)

(73) Assignee: Osaka University, Suita-Shi (JP)

( * ) Notice: Subject to any disclaimer, the term of this patent is extended or adjusted under 35 U.S.C. 154(b) by 344 days.

(21) Appl. No.: 11/515,351

(22) Filed: Sep. 1, 2006

(65) Prior Publication Data

US 2008/0217525 A1 Sep. 11, 2008

Related U.S. Application Data

(63) Continuation of application No. PCT/JP2005/002360, filed on Feb. 9, 2005.

(30) Foreign Application Priority Data

Mar. 2, 2004 (JP) .............................. 2004-057750

(51) Int. Cl.
*H01J 49/30* (2006.01)
(52) U.S. Cl. ...................... 250/298; 250/294; 250/287; 250/559.29; 250/208.1; 250/208.2

(58) Field of Classification Search ................. 250/294, 250/298, 287, 284, 559.29, 208.1, 208.2, 250/208.3, 208.4, 208.5, 208.6
See application file for complete search history.

(56) References Cited

U.S. PATENT DOCUMENTS

| | | | | |
|---|---|---|---|---|
| 3,523,185 | A | * | 8/1970 | Grossel et al. ............... 250/298 |
| 2004/0169137 | A1 | * | 9/2004 | Westphall et al. ........... 250/281 |
| 2005/0230615 | A1 | * | 10/2005 | Furutani et al. ............. 250/287 |

OTHER PUBLICATIONS

Suwa et al., "Manetophoretic Velocimetry of Manganese(II) in a Single Microdroplet in a Flow System under a High Gradient Magnetic Field Generated with a Superconducting Magnet", Oct. 2002, Anal. Chem., vol. 74, No. 19, pp. 5027-5032.*

* cited by examiner

*Primary Examiner*—Nikita Wells
*Assistant Examiner*—Hanway Chang
(74) *Attorney, Agent, or Firm*—Burr & Brown (57) ABSTRACT

A magnetic field gradient is generated in a space, and a microparticle is flied downward in the space, thereby applying a magnetic force from the magnetic field gradient onto the microparticle. Then, a velocity and an acceleration of the microparticle due to the magnetic force are measured, thereby measuring a mass of the microparticle on the measured velocity and a magnetic susceptibility of the microparticle.

21 Claims, 6 Drawing Sheets

MASS SPECTROMETRY AND MASS SPECTROSCOPE

BACKGROUND OF THE INVENTION

1. Field of the Invention

This invention relates to a mass spectrometry and a mass spectroscope.

2. Related Art

In a conventional mass spectrometry, a microparticle such as an ion to be analyzed is flied in a space where an electric field or an electromagnetic field is applied to the microparticle and thus, the resultant electrostatic force or Lorentz force acted on the micro particle to cause the change in motion of the micro particle and thus, measure the mass of the microparticle. In the conventional mass spectrometry, however, in order to apply the electrostatic force or the Lorentz force onto the microparticle, it is always required to ionize the microparticle. In this point of view, as of now, a variety of techniques are applied for the mass spectrometry and for example, the MALDI technique has been developed.

In the conventional techniques including the MALDI technique, however, the ionization efficiency of the microparticle is only 1% or below, so that the sensitivity of the mass spectrometry is very low and becomes remarkable if the mass of the microparticle is large. In this point of view, the mass of the microparticle to be analyzed in mass is restricted within a molecular weight range of $10^4$ Da or below. Therefore, the mass of the microparticle with a molecular weight of $10^5$ Da or over such as a protein molecule, an enzyme or a virus, of which the mass spectrometry is required in a molecular biology field and a clinical inspection field, can not be measured in mass.

SUMMARY OF THE INVENTION

It is an object of the present invention to provide a new mass spectrometry and a new mass spectroscope whereby a microparticle such as a molecule with an extremely large molecular weight can be analyzed in mass.

In order to achieve the above object, this invention relates to a mass spectrometry, comprising the steps of:

generating a magnetic field gradient in a space, flying a microparticle in the space, thereby applying a magnetic force from the magnetic field gradient onto the microparticle, and measuring a velocity and an acceleration of the microparticle due to the magnetic force, thereby measuring a mass of the microparticle on the velocity and the acceleration of the microparticle which are measured.

Also, this invention relates to a mass spectroscope, comprising:

a magnetic field gradient-generating means which is disposed in a space, and a velocity/acceleration-measuring means for measuring a velocity and an acceleration of a microparticle which is flied in the space under a magnetic force from a magnetic field gradient which is generated from the magnetic field gradient-generating means.

The inventors had intensely studied to achieve the above object, and as a result, found out the following fact of matters. When a microparticle to be analyzed in mass is flied in a low viscosity space under an atmospheric condition or a vacuum condition and a magnetic field gradient is generated in the low viscosity space, the magnetic force, originated from the magnetic field gradient, acts on the microparticle to change the flight velocity of the microparticle. By measuring the change of the flight velocity, i.e., the acceleration of the microparticle, therefore, the mass of the microparticle can be measured.

Concretely, if the magnetic force is designated by "Fm", and the viscous resistance force of the microparticle in the space is designated by "Fv", and the acceleration of gravity is designated by "g", and the acceleration of the microparticle is designated by "α", during the falling in the space of the microparticle, the following dynamic equation is satisfied:

$$Fm + mg - Fv = m\alpha \quad (1)$$

On the other hand, if the volume magnetic susceptibility of the microparticle is designated by "χ", and the vacuum permeability is designated by "$\mu_0$", and the volume of the microparticle is designated by "V", and the magnetic flux density of the space is designated by "B", the magnetic force Fm can be represented by the following equation:

$$Fm = (\chi/\mu_0) V B (dB/dx) \quad (2)$$

In this case, the magnetic field gradient is designated by "B(dB/dx)".

Moreover, if the viscosity of the space is designated by "η", and the radius of the microparticle is designated by "r", and the velocity of the microparticle is designated by "v", the viscous resistance force can be represented by the following equation:

$$Fv = 6\pi \eta r v \quad (3)$$

In the equation (2), the volume magnetic susceptibility χ of the microparticle, the volume V of the microparticle, the magnetic flux density B, and the magnetic field gradient dB/dx can be known in advance, the magnetic force Fm can be derived from the known factors and the equation (2). In the equation (3), the viscosity η of the space and the radius r of the microparticle can be known in advance, the viscous resistance force Fv can be derived from the known factors and the equation (3) by measuring the velocity v of the microparticle. Therefore, in addition to the magnetic force Fm and the viscous resistance force Fv, if the acceleration of the microparticle can be measured, the mass m of the microparticle can be measured.

Herein, even though the volume magnetic susceptibility χ of the microparticle is unknown, the mass m and the volume magnetic susceptibility χ of the microparticle can be measured simultaneously if the velocity and the acceleration of the microparticle are measured at at least two times because the simultaneous equation using the volume magnetic susceptibility χ and the mass m of the microparticle as parameters can be derived from the equation (1).

Moreover, if the terminal velocity of the microparticle is designated by "$v^0$" during the falling of the microparticle, by using the terminal velocity as an initial condition, the velocity v(t) at a time t can be derived from the equations (2) and (3) as follows:

$$v(t) = v^0 + (2\chi r^2/9\eta\mu_0)(BdB/dx)(t) - (m/6\pi r\eta)\alpha \quad (4)$$

Herein, in the derivation of the equation (4), it is supposed that the microparticle is perfectly sphere, and the equation $V = (4/3)\pi r^3$ is employed.

In the equation (4), if the terminal velocity of the microparticle is measured, and the velocity v(t) at the time t of the microparticle is measured, thereby calculating the acceleration α(t) of the microparticle, the intended mass m of the microparticle can be derived from the equation (4).

In the equation (4), even though the volume magnetic susceptibility χ of the microparticle is unknown, the mass m and the volume magnetic susceptibility $\chi$ of the microparticle can be measured simultaneously if the velocity and the acceleration of the microparticle are measured at at least two times because the simultaneous equation using the volume magnetic susceptibility $\chi$ and the mass m of the microparticle as parameters can be derived from the equation (4).

If the mass spectrometry of the present invention is performed under a vacuum condition within a pressure range of $2\times10^{-4}$ Pa or below, the viscosity $\eta$ of the space can be neglected. In this case, since in the equation (3), the viscous resistance force Fv can be almost zero, the equation (1) can be simply represented as follows:

$$Fm+mg=m\alpha \quad (5)$$

By measuring the acceleration of and the magnetic force to the microparticle, therefore, the intended mass m of the microparticle can be measured.

In the measurement of the mass m of the microparticle, equations (3) and (4) can be appropriately selected, respectively. Concretely, when the terminal velocity $v^0$ of the microparticle is known (measured), the equation (4) can be employed. When the terminal velocity $v^0$ is unknown, the equation (3) can be employed. Moreover, when the mass spectrometry is performed under the vacuum condition, the equation (5) can be employed.

In this way, according to the present invention, in the derivation of the mass m of the microparticle, it is never required to ionize the microparticle. Therefore, the decrease in measurement sensitivity of the mass m of the microparticle due to the low ionization efficiency thereof can be inhibited, and thus, the high sensitive mass spectrometry of the microparticle can be established. As a result, the mass of a molecule with an extremely large molecular weight within a range of $10^5$ or over such as a protein molecule, an enzyme or a virus, of which the mass spectrometry is required in a molecular biology field and a clinical inspection field, can be measured precisely.

The present invention further relates to a new mass analysis method of nano- and microparticles by using only a magnetophoretic force, which works on any particles in a magnetic field gradient. Magnetophoretic force exerted on a microparticle in solution has been utilized for the development of a magnetophoretic velocimetry of microparticles in solution, which affords a magnetic susceptibility of the particle. In a liquid, the relaxation time of a micrometer-sized particle, which is the required time to reach the terminal velocity, is shorter than $10^{-6}$ s. This means that any particles in liquids have to migrate practically with their terminal velocity. However, in a low-viscosity medium, such as air of ambient pressure, the relaxation time becomes as long as $10^{-3}$ to $10^{-1}$ s, which is much longer than that in a liquid. Therefore, it is expected that the acceleration of the particle in air is observable by a conventional optical technique and that the mass of the particle is measurable by using the equation of motion. Every ion, molecule, and particle has its own magnetic susceptibilities, reflecting the elemental composition and its spin states. Therefore, the present invention uses the magnetophoretic velocity of a particle under a high magnetic field gradient in an atmosphere for the simultaneous determination of its mass and magnetic susceptibility, without any ionization and high-vacuum conditions.

Magnetic fields have been used in various types of mass analyzers, such as a double-focusing sector instrument and an ion cyclotron resonance instrument; however, these techniques have used a Lorentz force generated in a homogeneous magnetic field, but not a magnetophoretic force generated by a magnetic field gradient. The mass analysis method in accordance with present invention has utilized only magnetophoretic force to modulate the falling velocity of a microparticle.

BRIEF DESCRIPTION OF THE DRAWINGS

For better understanding of the present invention, reference is made to the attached drawings, wherein

FIG. 4 are schematic drawings of an experimental setup for the magnetophoretic mass analysis, wherein FIG. 4(A) is the optical detection system to observe the velocity of a falling microparticle modulated by a magnetophoretic force, and FIG. 4(B) is an enlargement view of the laser desorption part and the atmospheric magnetophoresis region in the gap of pole pieces, FIG. 5 are observed oscillograms, wherein FIG. 5(A) is an oscillogram of the scattered light intensity from a falling 15 μm-diameter polystyrene particle in the absence of the permanent magnets, and FIG. 5(B) is an oscillogram of the scattered light intensity under the magnetic field gradient, the inset shows the definition of velocity and acceleration, where the velocity between the ith and the (i+1)th peaks is defined as $v_i$, and the acceleration between $v_i$ and $v_{i+1}$ is defined as ai,i+1.

DETAILED DESCRIPTION OF THE INVENTION

Details, other features and advantages of the present invention will be described with reference to the accompanying drawings.

Figure 1:
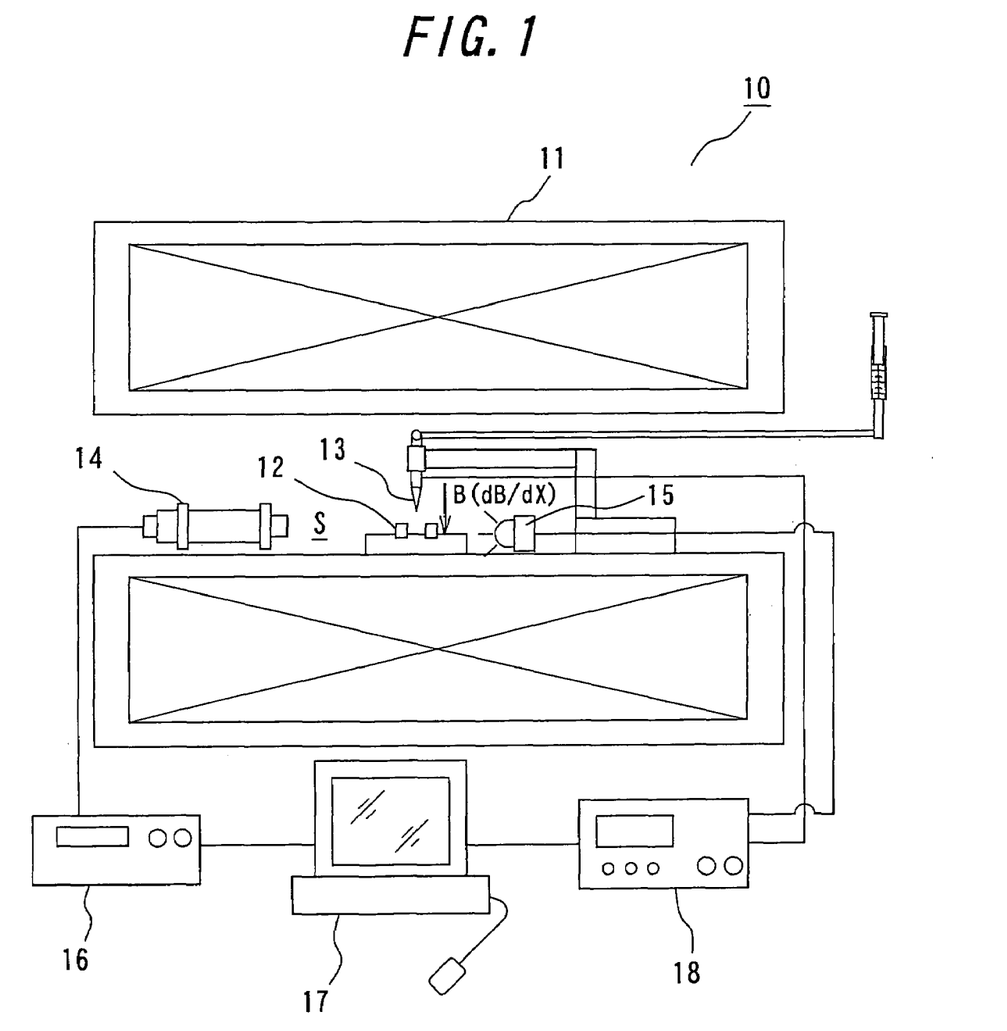
FIG. 1 is a structural view illustrating a typical example of mass spectrometry according to the present invention.

FIG. 1 is a structural view illustrating a mass spectrometry according to the present invention. The mass spectroscope 10 includes a super conducting magnet 11 and a pair of pole pieces 12 disposed in the inner space S of the mass spectroscope 10. The super conducting magnet 11 generates a magnetic field with a magnetic flux density of B in the inner space S, thereby generating the magnetic field gradient B(dB/dx) in between the pole pieces 12 in the direction along the arrow depicted in FIG. 1.

Moreover, the mass spectroscope 10 includes a liquid droplet generator 13 which is disposed above the almost center in between the pole pieces 12. In addition, the mass spectroscope 10 includes a CCD camera 14 and an electric flash 15 which are disposed so as to be opposed to one another via the pole pieces 12. A video recorder 16 and a PC 17 are connected to the CCD camera 14, and a wave form generator 18 and a PC 17 are connected to the liquid droplet generator 13 and the electric flash 15.

A given liquid droplet is emitted from the liquid droplet generator 13 with synchronized with the frequency of the voltage generated from the wave form generator 18 under the magnetic field gradient B(dB/dx). The emitted liquid droplet is photographed by the CCD camera 14 during the falling down of the liquid droplet under the light irradiation from the electric flash 15. The photographed image is recorded in the video recorder 16.

In this embodiment, the light irradiation for the liquid droplet is repeated several times from the electric flash 15 with synchronized with the voltage frequency from the wave form generator 18, and the liquid droplet is photographed by the CCD camera 14 via the PC 17 with synchronized with the light irradiation of the electric flash 15. Therefore, the falling of the liquid droplet can be photographed sequentially. In this case, the falling velocity of the liquid droplet can be derived at each photographing point from the photographing time interval (the light irradiation time interval of the electric flash 15) and the moving (falling) distance during the each photographing time interval, so that the acceleration of the liquid droplet can be derived at each photographing point (each photographing time interval) from the change in velocity of the liquid droplet thereat.

For example, if the moving distance between the photographing times t1 and t2 (the distance between the photographing points x(t1) and x(t2)) is L1, and the moving distance between the photographing times t2 and t3 (the distance between the photographing points x(t2) and x(t3)) is L2, the velocity $v_{12}$ of the liquid droplet at the center between the photographing points x(t1) and x(t2) can be represented by L1/(t2−t1), and the velocity $v_{23}$ of the liquid droplet at the center between the photographing points x(t2) and x(t3) can be represented by L2/(t3−t2). Therefore, the acceleration α (t2) at the photographing point x(t2) can be represented by (v23−v12)/(the time interval when the liquid droplet is moved (fallen) to the center between the photographing points x(t2) and x(t3) through the center between the photographing points x(t1) and x(t2). As a result, the velocity and the acceleration of the liquid droplet can be derived at a given photographing point, and thus, the mass m of the liquid droplet can be measured by using the equation (1).

The above-mentioned operation may be performed for all of the photographing points. In this case, the mass of the liquid droplet can be measured precisely by averaging masses measured at all of the photographing points of the liquid droplet.

The inner space S of the super conducting magnet 11 can be an atmospheric condition. In this case, the viscous resistance of the inner space S can be reduced, and the liquid droplet can be accelerated sufficiently by using the magnetic force from the magnetic field gradient, thereby enhancing the velocity and the acceleration of the liquid droplet and thus, enhancing the measuring accuracy of the mass of the liquid droplet. Moreover, if the inner space S is a vacuum condition within a pressure range of $2 \times 10^{-4}$ Pa or below, the viscous resistance of the inner space S can be almost neglected, so that the mass of the liquid droplet can be simply measured without the consideration of the viscous resistance.

The strength of the magnetic field gradient may be set to e.g., 100 $T^2/m$ or over. In this case, even though the size and weight of the liquid droplet are larger, the mass of the liquid droplet can be measured precisely because the velocity and the acceleration of the liquid droplet can be enhanced sufficiently.

EXAMPLES

Such an attempt was made as to perform a mass spectrometry for a liquid droplet (with a radius of about 29 μm) made of a manganese chloride solution (with a concentration of 0.3M) by using the mass spectrometry illustrated in FIG. 1. The magnetic flux density of the magnetic field generated from the super conducting magnet was set to 10 T, and the distance between the pole pieces 12 made of iron pieces was set to 300 μm. During the falling of the liquid droplet, the light irradiation from the electric flash 15 was performed at a frequency of 600 Hz.

Figure 2:
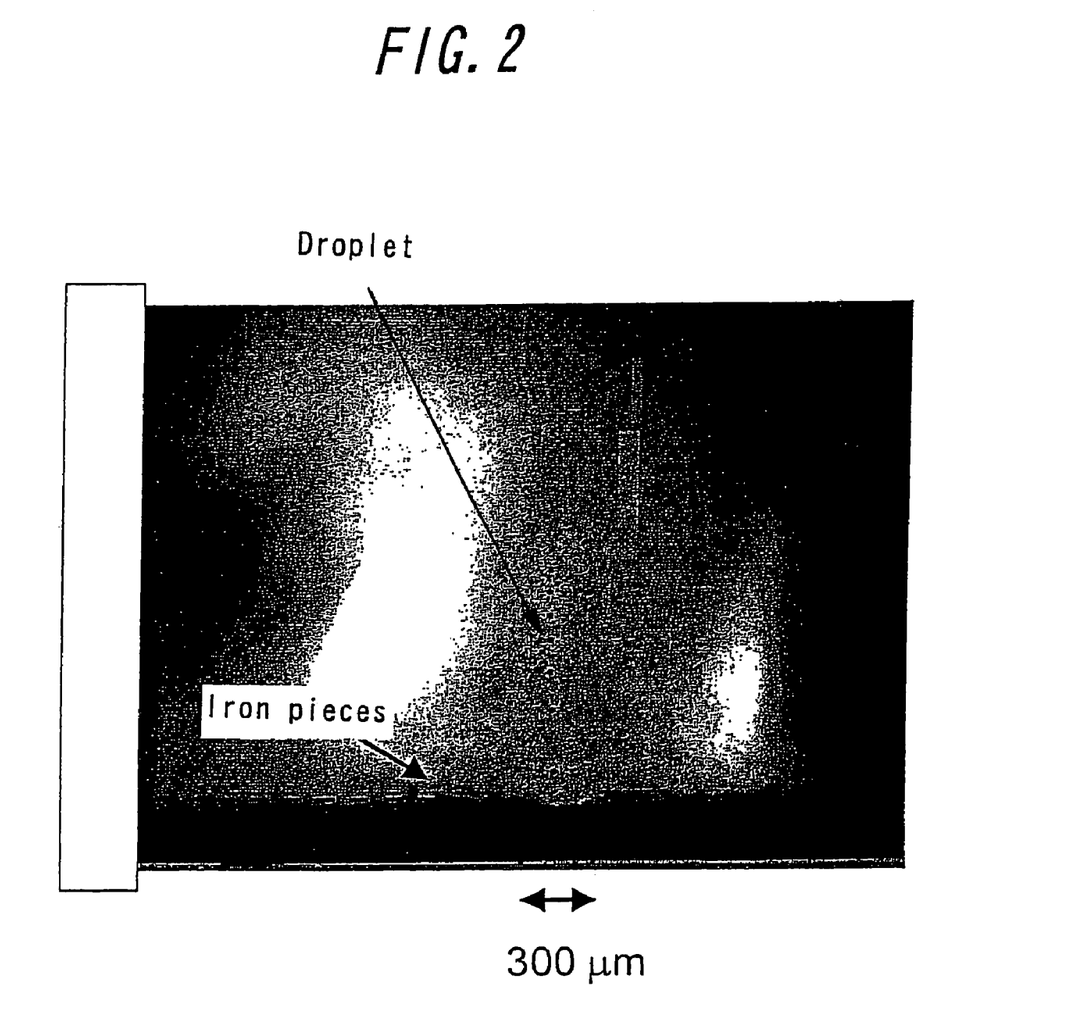
FIG. 2 is sequential photograph of a liquid droplet using an electric flash during the falling of the liquid droplet.

FIG. 2 is the track photograph of the liquid droplet during the falling which are photographed sequentially at the frequency of 600 Hz. As is apparent from FIG. 2, the velocity (the time interval in photographing) of the liquid droplet is increased toward the pole pieces 12.

Figure 3:
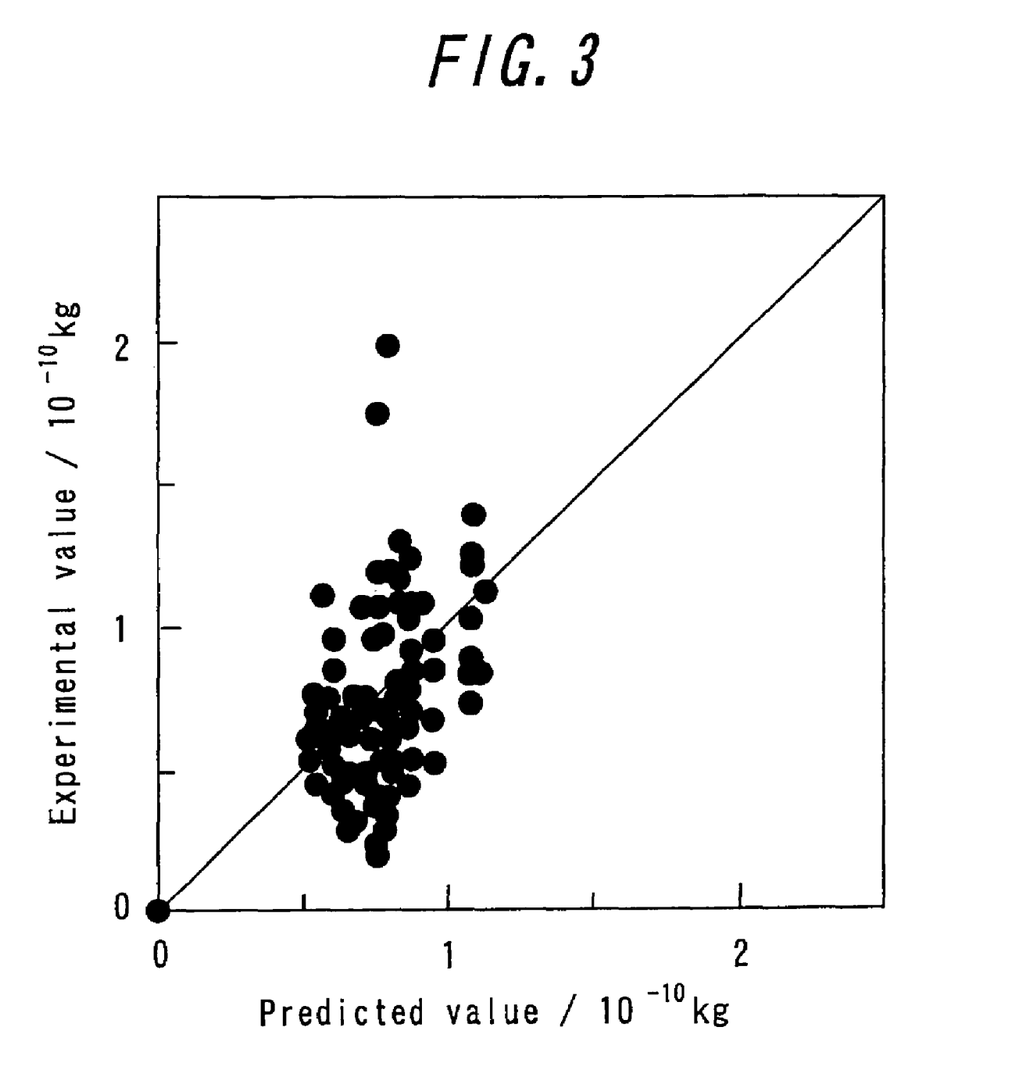
FIG. 3 is a graph showing the relation between the mass of the liquid droplet using the mass spectrometry and the mass spectroscope of the present invention and the predicted mass of the liquid droplet.

FIG. 3 is a graph showing the relation between the mass (experimental value) of the liquid droplet measured according to the mass spectrometry of the present invention as mentioned above and the predicted mass of the liquid droplet on the size of the liquid droplet. As is apparent from FIG. 3, the experimental mass of the liquid droplet using the mass spectrometry and the mass spectroscope of the present invention are coincident with the predicted mass of the liquid droplet. Therefore, it is turned out that the mass of the liquid droplet can be measured precisely by using the mass spectrometry and the mass spectroscope of the present invention.

Although the mass of the liquid droplet is measured in the above embodiment, the present invention can be applied for other microparticles such as a solid microparticle as described below.

Figure 4:
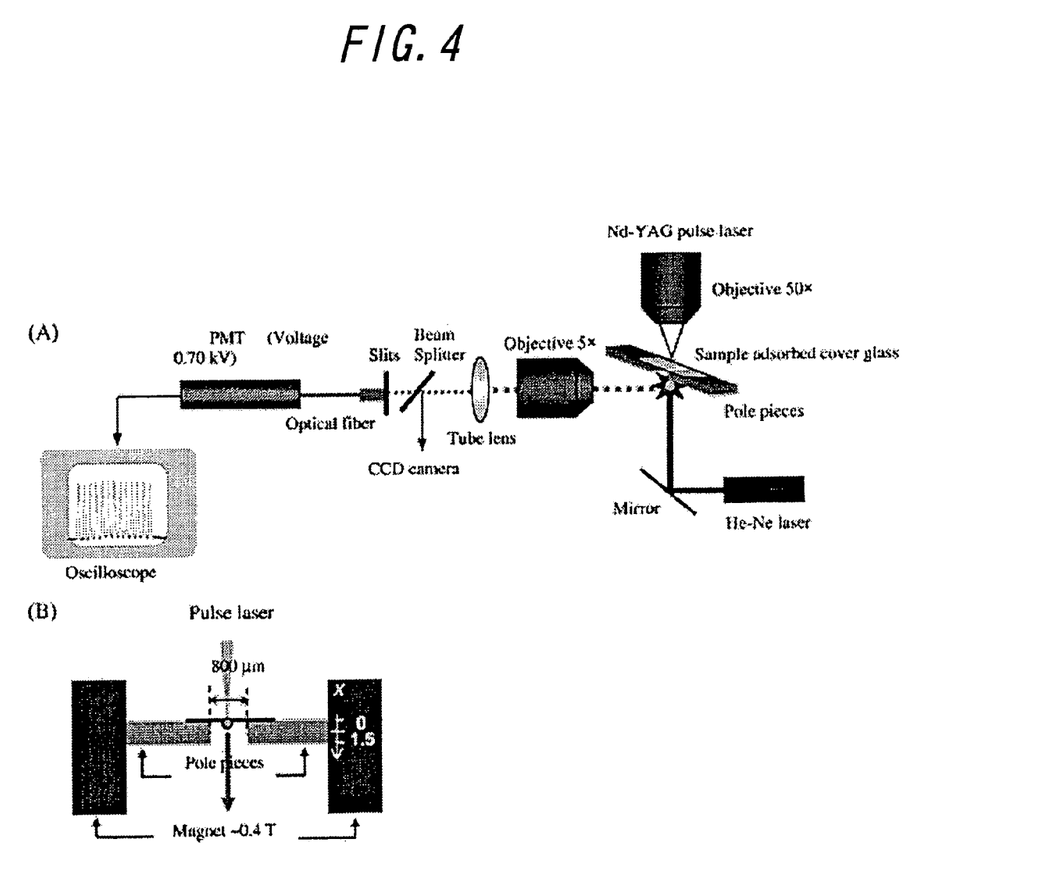

FIG. 4 show schematic drawings of an experimental setup for the magnetophoretic mass analysis according to the present invention, wherein FIG. 4(A) is the optical detection system to observe the velocity of a falling microparticle modulated by a magnetophoretic force, and FIG. 4(B) is an enlargement view of the laser desorption part and the atmospheric magnetophoresis region in the gap of pole pieces.

(Sample Preparation)

Polystyrene particles of two different sizes (10 and 15 μm in diameter) were used as test samples. The polystyrene particles (Polysciences, Inc., Japan) were dispersed in water at a concentration of (1.9 to 30)×$10^4$ particles/mL. A small droplet of the dispersion was put onto a cover glass (Polysciences, Inc, Japan), and the solvent was evaporated in a reduced pressure desiccator to leave the polystyrene particles adsorbed on the cover glass. Water was purified by a Milli-Q system (Millipore, Billerica, Mass.).

(Apparatus)

As shown in FIGS. 4(A), 4(B), a magnetic field gradient was generated by a pair of pole pieces (iron chips) with 3 mm thickness, 5 mm width, and 13 mm length, which were stuck to Nd—Fe—B magnets (0.45 T, NeoMag, Japan) individually. The gap of the pole pieces was 800 μm, as shown in FIG. 4(B). The magnetic field in the gap of the pole pieces was measured along a vertical center axis by a Gauss meter (HGM 3000P, ADS Corp, Japan) with a small probe (FS-7S, ADS Corp, Japan) and also simulated by a finite element method using commercial software (ANSYS, Inc).

A mask with multiple slits was fabricated on a glass slide coated with 100 nm Au/5 nm Cr (EMF Corp, New York) by a computer-controlled laser ablation method, which had been developed previously for the fabrication of a microquadrapole gold electrode for a dielectorphoresis of microparticles in an aqueous solution. The slit array mask used in the present study had nine slits, each 123 μm in width and 5 mm in length. The distance between adjacent slits was 507 μm. The slits were set horizontally at the image plane of falling particles observed through an optical system with an objective (5×).

A polystyrene particle on the underside of the cover glass was selectively desorbed by a thermal shock of single-shot laser pulse (532 nm, 5 to 7 ns pulse duration, 1.1 mJ/pulse) from a Nd:YAG laser device (MiniLase-II 20ST, New Wave Research, Japan) and dropped into the gap of pole pieces attached to the magnets. To detach a particle selectively, a pulsed laser light from the laser device was focused at the lower surface of the cover glass through a beam expander, a square mask, a tube lens, and an objective of 50× magnification. The irradiation area was controlled by the square mask. A beam of a He—Ne laser (632.8 nm, 0.80 mm of beam waist, 15 mW, Melles Griot, U.S.A.), which was directed upward in reverse to the falling direction of the particle, as shown in FIGS. 4(A), 4(B), irradiated the falling particles. The laterally scattered light was collected by an objective of 5× magnification focused on the slit array mask attached to the end of an optical fiber (6 mm in diameter) by a tube lens and then introduced into a photomultiplier tube (PMT) (R374, Hamamatsu Photonics, Japan) as a photo detector. Photocurrent signals from the PMT were stored in a digital oscilloscope (DS-4262, IWATSU, Japan). The falling velocities of particles were observed in the region of x=1.3 to 2.1 mm, as shown in FIG. 4(B). The velocities and accelerations of the particles were calculated from the recorded oscillogram of the scattered light.

(Theory)

First, the theoretical background of the new magnetophoretic velocity modulation mass analysis of a microparticle in accordance with the present invention is described. The inventors defined the direction of gravity as the x direction and the center of the gap of the pole pieces as x=0 (FIG. 4(B)). The x component of the magnetophoretic force working on a particle, $F_M$, in the magnetic field gradient, dB/dx, can be expressed as $$F_M = \frac{\chi}{\mu_0} V B \frac{dB}{dx} \quad (6)$$

where $\chi$ and V are the volume magnetic susceptibility and the volume of a particle, respectively, and $\mu_0$ is the magnetic permeability of a vacuum. The equation of motion for a falling particle in a magnetic field gradient can be written as $$F_M - F_G = F_D = ma \quad (7)$$

where $F_G$=mg is the gravity, m is the mass of the particle, g is the gravitational acceleration, a is the acceleration of the particle, and $F_D$ is the viscous drag force in air. The Stokes equation for the viscous drag force, $F_D$=−6πηrv, is applicable to this system, in which η is the viscosity of air (1.8×10$^{-5}$ Pa s), r is the radius of the particle, and v is the velocity of the particle. Substitution of equation (6) into equation (7) yields $$(a-g)\frac{m}{r} - \frac{1}{\mu_0} B \frac{dB}{dx} \frac{\chi}{r} V = -6\pi\eta v \quad (8)$$

Equation (8) suggests that the mass, m, and magnetic susceptibility, $\chi$, can be obtained simultaneously when the shape of the particle is approximated by a sphere with a hydrodynamic radius determined by a free-fall velocity and more than two pairs of observed values for velocity and acceleration are available from appropriate experiments.

(Results)

Figure 5:
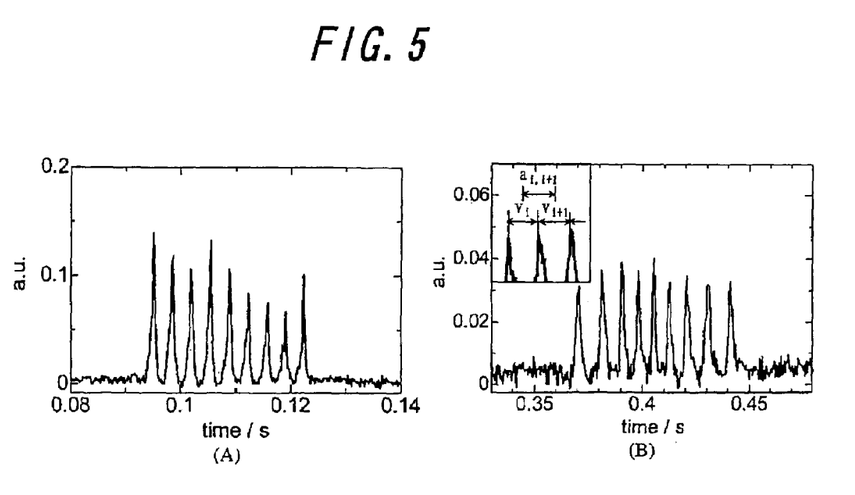

As the first experiment, the reliability of the laser desorption method of a single polystyrene particle from a cover glass was confirmed, and the velocity of the falling polystyrene particle was measured in the absence of the magnetic field gradient to investigate whether the particle was falling at the terminal velocity in the observing region. FIG. 5(A) shows a typical oscillogram of the scattered light intensity through a nine-slit mask from a falling particle 15 μm diameter in the absence of the permanent magnets. The scattering light from the falling particle at the object plane of the objective lens (5×) could be detected by the PMT only when it was focused at one of the apertures in the slit array mask on the image plane of the objective lens. The direction of the line slits was set perpendicular to gravity. Therefore, the interval between the ith and the (i+1)th signals in the observed nine spike signals, $\Delta t_i$, in the oscillogram corresponded to the time that the scattering light image from a particle moved from the ith slit to the (i+1)th slit in the mask at the image plane (507 μm), that is, the time that the particle fell for the conjugated ⅕ distance, $\Delta d$ (101 μm), on the object plane in the present measurements using the objective with 5× magnification. The velocities for two neighboring spikes were calculated by dividing $\Delta d$ by the intervals. As shown in the inset of FIG. 5(B), the inventors defined the velocity obtained from $\Delta t_i$ as $v_i$ and the acceleration calculated from $v_i$ and $v_{i+1}$ as $a_{i,\,i+1}$. The observed velocities of the falling particle in the absence of magnets were almost constant at 8.06 mm s$^{-1}$ in the average for 15 μm particles and were close to the expected terminal velocity of 7.15 mm s$^{-1}$.

Figure 6:
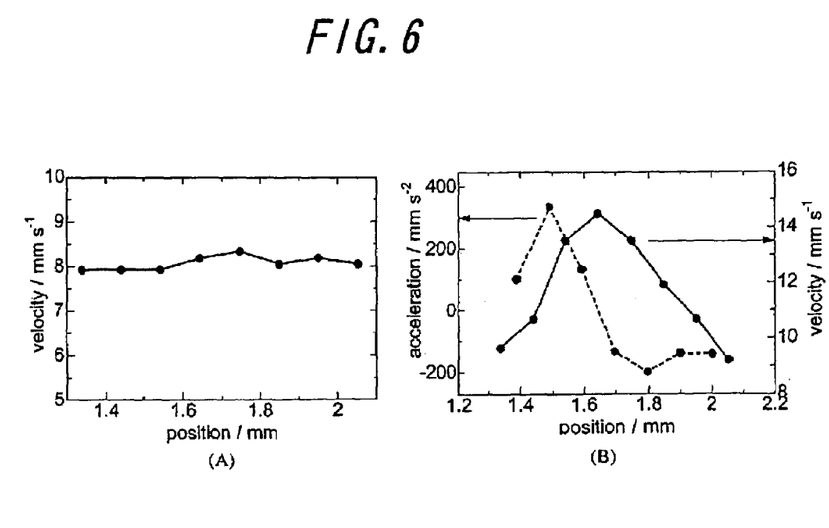
FIG. 6(A) is a graph showing falling velocities of a 15 μm-diameter polystyrene particle in the absence of magnets obtained from the oscillogram of FIG. 2A, which was close to the terminal velocity.
FIG. 6(B) is a graph showing modulated falling velocities of the 15 μm particle by the magnetic field gradient and accelerations obtained from FIG. 2B plotted against the position of the particle on the x axis.

FIG. 5(B) shows a typical oscillogram of the scattered light intensity from a falling 15 μm polystyrene particle under the magnetic field gradient. In FIG. 5(B), it was obvious that the intervals between the spikes were not constant, but were shorter, around 0.40 s, which referred to the region of the highest magnetic field gradient. Velocities and accelerations of the particle were calculated from the intervals of the scattered light intensity profile and plotted against the vertical position of the particle in FIG. 6(3). The velocity showed a maximum around x=1.64 mm; the acceleration was positive before x=1.64 mm and negative after x=1.64 mm. In the central region of the pole pieces with a homogeneous magnetic field (x=0 mm), no magnetic force worked on the particle. However, near the edge of the pole pieces (x=1.5 mm), the diamagnetic polystyrene particle was pushed out from the gap by a magnetophoretic force, and the velocity was accelerated.

Figure 7:
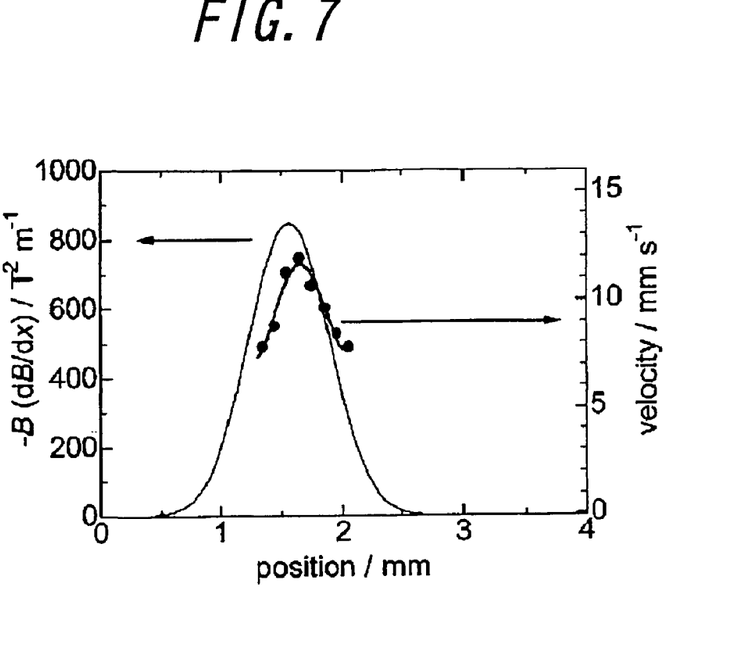
FIG. 7 is a graph showing a simulated product of the magnetic flux density and its gradient, B(dB/dx), and the observed falling velocities of the 15 μm-diameter particle plotted against the position on the x axis, the gap between both maximums indicates the modulation effect of the magnetophoretic force.

FIG. 7 shows the comparison between the variation of B(dB/dx) obtained by the simulation and the observed velocities. In FIG. 7, the maximum position of the velocity was shifted to a larger x position from that of −B(dB/dx). If the situation is the steady-state migration such as that in liquids, in which the acceleration term of equation (7) is negligible, both maximums must be consistent. Therefore, the observed disagreement is definite evidence of the non-steady-state migration of the particle, indicating that the right-hand side of equation (7) cannot be neglected. The non-steady-state migration has also been observed in the case of the magnetophoretic effect on the falling velocity of droplets in an atmosphere. The reason is that the relaxation time for the translational motion in air of a 15 μm-diameter particle is as long as $7.3 \times 10^{-4}$ s, which is much longer than the response time of the measurement electronics, including the PMT, whose response time is shorter than 100 ns.

The inventors examined two kinds of data analyses to obtain mass and magnetic susceptibility of the particles simultaneously. As the first method, the inventors used two pairs of accelerations and velocities at x=1.5 mm, where −B(dB/dx) was maximum, and at x=2.0 mm, where −B(dB/dx) was nearly equal to zero. At the former position, non-steady-state falling behavior could be clearly observed. Concretely, the values of the acceleration $a_{2,3}$ and the averaged velocity of $v_2$ and $v_3$ and another set of the values of the acceleration $a_{7,8}$ and the averaged velocity of $v_7$ and v8 were used for the calculation of the mass and the magnetic susceptibility of the particle by using equation (8).

As the second method, equation (8) was rewritten as $$\frac{v}{B\frac{dB}{dx}} = -\frac{m}{6\pi\eta r}\frac{(a-g)}{B\frac{dB}{dx}} + \frac{\chi V}{6\pi\eta\mu_0 r} \quad (9)$$

Figure 8:
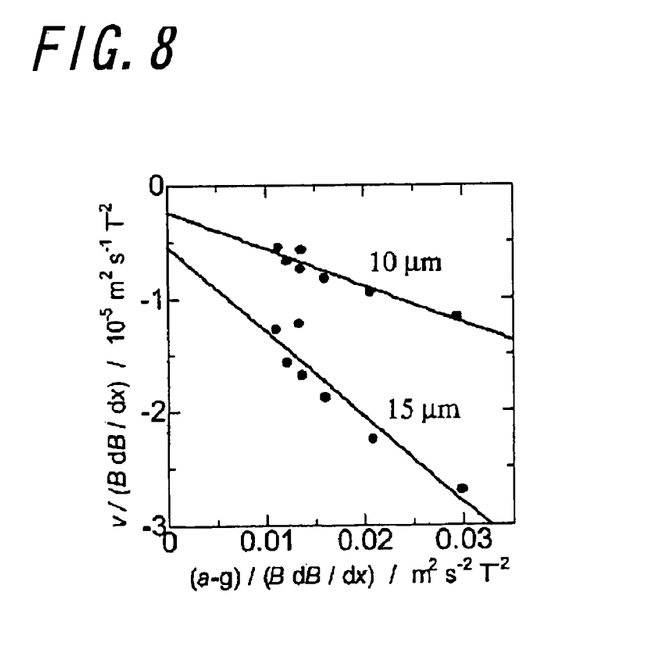
FIG. 8 is a graph showing typical results of the plot of v/B(dB/dx) vs (a−g)/(B dB/dx) according to eq 4 for the cases of 10 and 15 μm polystyrene particles, the observed values of m and $\chi$ listed in Table 1 were determined by using the slope and the intercept of the fitted straight lines as the second method.

When the value of the left-hand side term of equation (9) was plotted against the value of (a−g)/(B dB/dx), as shown in FIG. 8, the slope and the intercept referred to −m/6πηr and χV/6πημ₀r in equation (9), respectively. The radius, r, of an individual particle can be related to the mass m by equation (10)

$$r = \left(\frac{3m}{4\pi\rho}\right)^{1/3} \quad (10)$$

where ρ is the density of polystyrene (1.05 g/cm³). Finally, the mass and magnetic susceptibility could be determined by substitution of equation (10) into the slope, −m/6πηr and the intercept, χV/6πημ₀r, obtained from FIG. 8. In this method, all velocities and accelerations observed in a measurement could be used to obtain m and χ without any selection of two sets of data for the velocity and the acceleration, which was done in the first method. Therefore, the second method might be more rigorous than the first method. Equation (10) was also used for the calculation in the first method. The results are summarized in Table 1. The observed values for m and χ were close to the expected mass from the nominal averaged values of the diameter and the magnetic susceptibility of polystyrene.

TABLE 1

[Observed and Calculated Values of Mass m and Magnetic Susceptibility χ for Polystyrene Microparticles under the Concept That the Radius Is Unknown]

| diameter | first method | | second method | | expected values | |
|---|---|---|---|---|---|---|
| | m, ng | χ, 10⁻⁶ | m, ng | χ, 10⁻⁶ | m, ng | χ, 10⁻⁶ |
| 10 μm | 0.95 ± 0.37 | −7.55 ± 1.08 | 0.92 ± 0.29 | −12.1 ± 0.1 | 0.51 ± 0.18 | −8.21 |
| 15 μm | 2.71 ± 0.55 | −8.49 ± 1.28 | 2.48 ± 0.45 | −12.1 ± 2.1 | 34 ± 0.98 | −8.21 |

All values obtained from both methods were examined by Thompson's method (95% confidence interval).

Incidentally, the improvement of the measurement system to get more accurate results can be achieved by increasing the number of the slits in the mask, by adapting a larger magnetic field gradient, by increasing the sensitivity to detect the forward scattered light, and by stabilizing the environment of the falling particle covering the magnetophoretic region with walls.

Thus, with the present invention, an innovative mass analysis principle of microparticles was achieved by applying the magnetophoretic force to the falling particle in an atmosphere in combination with the pulsed laser desorption method and the scattered laser detection method. The present method has no need for an ionization of samples and a high vacuum and can afford a mass and a magnetic susceptibility of a single particle simultaneously, whether it is paramegnetic or diamagnetic. This method will be promising for the mass analysis of bioparticles, especially of large molecular weight proteins, DNA, and even whole cells, as well as for the characterization of various types of nanoparticles.

Although the present invention was described in detail with reference to the above examples, this invention is not limited to the above disclosure and every kind of variation and modification may be made without departing from the scope of the present invention.

INDUSTRIAL APPLICABLE FIELD

The present invention may be employed in a magnetic component measurement field of floating particle and a lung disease-related measurement field. The present invention may be also employed in a cellular pathologic diagnosis and a molecular diagnosis of abnormal chromosome and protein of a molecular biology field and clinical inspection field. Moreover, the present invention may be employed in a mass spectrometry of a molecule with a molecular weight of 10⁵ Da or over such as a protein molecule, an enzyme or a virus.

The invention claimed is:

1. A mass spectrometry, comprising the steps of:
generating a magnetic field gradient in a space,
applying a magnetic force from said magnetic field gradient onto said microparticle, and
measuring a velocity and an acceleration of said microparticle due to said magnetic force, thereby measuring a mass of said microparticle based on said velocity and said acceleration of said microparticle which are measured, wherein said mass of said microparticle is derived from the following equation:

$v(t)=v^0+(2\chi r^2/9\eta\mu_0)(BdB/dx)(t)-(m/6\pi r\eta)a$ (v(t): a velocity of said microparticle at a time t, $v^0$: a terminal velocity of said microparticle, $\chi$: a volume magnetic susceptibility of said microparticle, r: a radius of said microparticle, $\eta$: a viscosity of said space, $\mu_0$: a vacuum permeability, B: a magnetic flux density in said space, B(dB/dx): a strength of said magnetic field gradient, m: said mass of said microparticle, $\alpha$(t): an acceleration of said microparticle at a time t).

2. The mass spectrometry as defined in claim 1, wherein said space is an atmospheric condition.

3. The mass spectrometry as defined in claim 1, wherein said space is a vacuum condition.

4. The mass spectrometry as defined in claim 3, wherein a pressure in said space is within a range of $2\times10^{-4}$ Pa or below.

5. The mass spectrometry as defined in claim 1, wherein a strength of said magnetic field gradient is within a range of 100 $T^2$/m or greater.

6. The mass spectrometry as defined in claim 1, wherein said microparticle is a liquid droplet.

7. The mass spectrometry as defined in claim 1, wherein said microparticle is a molecule with a molecular weight of $10^5$ Da or over.

8. The mass spectrometry as defined in claim 1, wherein desorption for said microparticle from an under surface of a stage is triggered by a thermal shock of a single-shot laser pulse.

9. The mass spectrometry as defined in claim 1, wherein measuring a velocity and an acceleration of said microparticle is executed with measurement of laterally scattered light from said microparticle of a laser beam directed upward in reverse to said direction of said microparticle, by a photo detector through a slit array.

10. A mass spectrometry, comprising the steps of:
generating a magnetic field gradient in a space,
applying a magnetic force from said magnetic field gradient onto said microparticle, and
measuring a velocity and an acceleration of said microparticle due to said magnetic force, thereby measuring a mass of said microparticle based on said velocity and said acceleration of said microparticle which are measured,
wherein said space is an atmospheric condition, and
wherein said mass of said micro particle is derived from the following equation:

$$(a-g)\frac{m}{r} - \frac{1}{\mu_0}B\frac{dB}{dx}\frac{\chi}{r}V = -6\pi\eta v$$

(v: a velocity of said microparticle, a: an acceleration of said microparticle, g: an acceleration of gravity, $\chi$: a volume magnetic susceptibility of said micro-particle, r: a radius of said microparticle, $\eta$: a viscosity of said space, $\mu_0$: a vacuum permeability, B: a magnetic flux density in said space, B(dB/dx): a strength of said magnetic field gradient, m: said mass of said microparticle, V: a volume of said microparticle).

11. The mass spectrometry as defined in claim 10, wherein said mass, m, and said volume magnetic susceptibility of said micro-particle, $\chi$ are determined simultaneously, by using measured two pairs of a velocity and an acceleration of said microparticle.

12. A mass spectroscope, comprising:
a magnetic field gradient-generating means which is disposed in a space;
a velocity/acceleration-measuring means for measuring a velocity and an acceleration of a microparticle which is under a magnetic force from a magnetic field gradient which is generated from said magnetic field gradient-generating means; and
a trigger means for desorption of said microparticle from an under surface of a stage for flying using a thermal shock of a single-shot laser pulse.

13. The mass spectroscope as defined in claim 12, wherein said magnetic field gradient-generating means includes a magnet and a pair of pole pieces which are disposed in a magnetic field generated from said magnet.

14. The mass spectroscope as defined in claim 12, wherein said velocity/acceleration-measuring means includes a photographing means for photographing a track of said microparticle sequentially.

15. The mass spectroscope as defined in claim 12, wherein said space is an atmospheric condition.

16. The mass spectroscope as defined in claim 12, wherein said space is an vacuum condition.

17. The mass spectroscope as defined in claim 16, wherein a pressure in said space is within a range of $2\times10^{-4}$ Pa or below.

18. The mass spectroscope as defined in claim 12, wherein a strength of said magnetic field gradient is within a range of 100 $T^2$/m or greater.

19. The mass spectroscope as defined in claim 12, wherein said microparticle is a liquid droplet.

20. The mass spectroscope as defined in claim 12, wherein said microparticle is a molecule with a molecular weight of $10^5$ Da or greater and is one of ionized and non ionized.

21. The mass spectroscope as defined in claim 12, wherein said velocity/acceleration-measuring means includes:
a laser means for lighting said microparticle by a laser beam directed upward in reverse to the direction of said microparticle; and
a photo detector for detecting a laterally scattered light from said microparticle of a laser beam of said laser means, through a slit array.

* * * * *